United States Patent
Schreiber

(10) Patent No.: US 9,851,485 B2
(45) Date of Patent: Dec. 26, 2017

(54) HOLLOW OPTICAL WAVEGUIDE WITH OPENINGS, PARTICULARLY FOR SUPPLYING A PHOTOBIOREACTOR WITH LIGHT AND NUTRIENTS

(71) Applicant: Airbus Defence and Space GmbH, Ottobrunn (DE)

(72) Inventor: Robert Schreiber, Gräfelfing (DE)

(73) Assignee: Airbus Defence and Space GmbH, Ottobrunn (DE)

( * ) Notice: Subject to any disclaimer, the term of this patent is extended or adjusted under 35 U.S.C. 154(b) by 0 days.

(21) Appl. No.: 15/141,174

(22) PCT Filed: Oct. 14, 2014

(86) PCT No.: PCT/DE2014/000506
§ 371 (c)(1),
(2) Date: Apr. 28, 2016

(87) PCT Pub. No.: WO2015/062563
PCT Pub. Date: May 7, 2015

(65) Prior Publication Data
US 2016/0349426 A1    Dec. 1, 2016

(30) Foreign Application Priority Data
Oct. 28, 2013    (DE) .................. 10 2013 017 742

(51) Int. Cl.
*G02B 6/00*    (2006.01)
*F21V 8/00*    (2006.01)
*C12M 1/00*    (2006.01)

(52) U.S. Cl.
CPC ............. *G02B 6/001* (2013.01); *C12M 21/02* (2013.01); *C12M 31/08* (2013.01); *C12M 43/08* (2013.01); *G02B 6/0096* (2013.01)

(58) Field of Classification Search
CPC ..................................................... C12M 21/02
See application file for complete search history.

(56) References Cited

U.S. PATENT DOCUMENTS

| | | | |
|---|---|---|---|
| 4,324,068 A * | 4/1982 | Anthony | C12M 21/02 47/1.4 |
| 6,174,720 B1 * | 1/2001 | Oxley | C12M 21/02 435/293.1 |

(Continued)

FOREIGN PATENT DOCUMENTS

| | | |
|---|---|---|
| CN | 102933894 A | 2/2013 |
| DE | 29723561 U1 | 11/1998 |

(Continued)

*Primary Examiner* — Rhonda Peace
(74) *Attorney, Agent, or Firm* — Lorenz & Kopf, LLC

(57) ABSTRACT

An elongated hollow optical waveguide (1) is described, as can be used in particular in a photobioreactor for supplying phototrophic organisms both with light and with nutrients. The optical waveguide (1) has a casing (3) made from transparent plastic, which surrounds a hollow core (5). The hollow core has a diameter of at least 1 mm, preferably at least 3 mm or at least 1 cm. A plurality of openings (7) with a diameter of at least 0.5 mm, preferably at least 1 mm, is constructed in the casing (3). Light can propagate through the transparent casing and preferably exit laterally (19) along the entire optical waveguide (1). Nutrients (15) can be conveyed through the hollow core (5) into the interior of the photobioreactor. Conversely, portions of the solution, to which organisms have been added, can also be sucked through the hollow core (5), for example in order to analyze the same.

12 Claims, 2 Drawing Sheets

(56) References Cited

U.S. PATENT DOCUMENTS

| | | | | |
|---|---|---|---|---|
| 6,584,714 B1* | 7/2003 | Wehrmann | G02B 6/001 | 40/542 |
| 6,606,431 B2* | 8/2003 | Unsworth | G02B 6/001 | 385/147 |
| 6,673,532 B2* | 1/2004 | Rao | C12M 23/12 | 435/287.1 |
| 6,887,692 B2* | 5/2005 | Paterek | C02F 3/2853 | 435/168 |
| 7,033,570 B2* | 4/2006 | Weimer | C09C 1/48 | 252/373 |
| 7,895,790 B2* | 3/2011 | Lin | C12M 21/02 | 435/289.1 |
| 8,183,032 B2* | 5/2012 | Frank | C12M 21/02 | 435/257.1 |
| 8,277,984 B2* | 10/2012 | Logan | H01M 4/8605 | 429/401 |
| 8,716,010 B2* | 5/2014 | Csanyi | C12M 21/02 | 435/289.1 |
| 8,722,396 B2* | 5/2014 | Kassebaum | C12M 21/02 | 435/257.1 |
| 9,523,070 B2* | 12/2016 | Erickson | C12M 21/02 | |
| 2003/0188740 A1* | 10/2003 | Tribelsky | C02F 9/00 | 128/200.14 |
| 2005/0064577 A1* | 3/2005 | Berzin | B01D 53/85 | 435/266 |
| 2006/0087864 A1* | 4/2006 | Peng | B60Q 1/56 | 362/554 |
| 2009/0203116 A1* | 8/2009 | Bazaire | C12M 21/02 | 435/257.1 |
| 2010/0055765 A1* | 3/2010 | Frank | C12M 21/02 | 435/257.1 |
| 2010/0097822 A1* | 4/2010 | Mersch | A61B 5/0059 | 362/572 |
| 2010/0144023 A1* | 6/2010 | Weaver | C12M 21/02 | 435/292.1 |
| 2010/0190227 A1* | 7/2010 | Dauth | C12M 21/02 | 435/168 |
| 2010/0273252 A1* | 10/2010 | Lin | C12M 21/02 | 435/292.1 |
| 2011/0107664 A1* | 5/2011 | Rancis | A01G 33/00 | 47/1.4 |
| 2011/0318819 A1* | 12/2011 | Legendre | C12M 21/02 | 435/286.1 |
| 2012/0203714 A1* | 8/2012 | Gonzalez | A01G 33/00 | 705/500 |
| 2012/0247008 A1* | 10/2012 | Gonzalez | A01G 33/00 | 47/1.4 |
| 2012/0282677 A1* | 11/2012 | Brod | C12M 21/02 | 435/257.1 |
| 2012/0288928 A1* | 11/2012 | Jung | C12M 21/02 | 435/292.1 |
| 2013/0077345 A1* | 3/2013 | Sato | G02B 6/0061 | 362/609 |
| 2013/0286380 A1* | 10/2013 | Selker | G01J 3/44 | 356/51 |
| 2013/0302869 A1* | 11/2013 | Erickson | C12M 21/02 | 435/160 |
| 2014/0243572 A1* | 8/2014 | Straub | B01D 63/04 | 585/802 |
| 2016/0002580 A1* | 1/2016 | Erickson | C12M 21/02 | 435/134 |
| 2016/0201020 A1* | 7/2016 | Gobel | C12M 31/08 | 435/292.1 |
| 2016/0349426 A1* | 12/2016 | Schreiber | C12M 21/02 | |

FOREIGN PATENT DOCUMENTS

| | | | | |
|---|---|---|---|---|
| EP | 2520642 A1 | 11/2012 | | |
| EP | 2581641 A4 * | 8/2016 | | G02B 6/0061 |

* cited by examiner

HOLLOW OPTICAL WAVEGUIDE WITH OPENINGS, PARTICULARLY FOR SUPPLYING A PHOTOBIOREACTOR WITH LIGHT AND NUTRIENTS

CROSS-REFERENCE TO RELATED APPLICATIONS

This is a continuation of International Application No. PCT/DE2014/000506, filed Oct. 14, 2014, which application claims priority to German Application No. 10 2013 017 742.1, filed Oct. 28, 2013, which are hereby incorporated by reference in their entirety.

TECHNICAL FIELD

The embodiments described herein relate to a specially constructed hollow optical waveguide and an optical-waveguide arrangement. Furthermore, the embodiments relate to a photobioreactor, in which one such optical waveguide or one such optical-waveguide arrangement is used. In addition embodiments relate to a method for operating a photobioreactor and a method for manufacturing an optical waveguide that can advantageously be used in a photobioreactor.

BACKGROUND

In addition, other objects, desirable features and characteristics will become apparent from the subsequent summary and detailed description, and the appended claims, taken in conjunction with the accompanying drawings and this background.

Phototrophic organisms are microbes, e.g. in the form of microorganisms, which can use light directly as an energy source for their metabolism. For example, phototrophic organisms include certain plants, mosses, micro-algae, macro-algae, cyanobacteria, and purple bacteria.

It may be desirable for different use purposes to be able to produce biomass, for example in the form of algae, in large quantities and inexpensively. For example, such biomass can be used for creating alternative biofuels, e.g. for the transport sector.

So-called bioreactors are used in order to be able to create biomass on an industrial scale. A bioreactor is a plant for producing organisms outside of their natural environment and within an artificial technical environment. So-called photobioreactors are used in order to cultivate phototrophic organisms. A photobioreactor provides the phototrophic organisms with both light and nutrients, for example $CO_2$ and a suitable nutrient solution, so that the phototrophic organisms can correspondingly create biomass.

In general, both open and closed systems are known for photobioreactors. Each of these types of photobioreactors has certain advantages and disadvantages.

In open photobioreactor systems, sometimes also termed open ponds, phototrophic organisms are cultivated in a controlled manner in open reservoirs or ponds. In this case, for the most part a nutrient solution or culture suspension, which contains all of the required nutrients and $CO_2$ for the relevant organism, are supplied in a circuit and illuminated for the most part directly by the sun from the open surface.

Possible advantages of such open photobioreactor systems are a relatively small technical outlay and low power consumption.

However, illumination solely by means of the upwardly open surface entails that only small volumes can be supplied with sufficient light. For the most part, light can only penetrate to a depth of a few centimeters into a nutrient solution to which organisms have been added. The depth of such open photobioreactor systems is therefore generally limited to 20 to 30 cm. The low average light influx leads to low areal growth rates. Thus, a correspondingly large area must be provided for open photobioreactor systems. As a result, costs are increased considerably for such photobioreactors, particularly in densely populated regions.

In addition, pronounced evaporation and therefore salinity effects may result at the exposed surface. Furthermore, a considerable quantity of $CO_2$ can also diffuse into the atmosphere via the exposed surface. Conversely, contaminants may enter an open photobioreactor via the exposed surface, contaminate the photobioreactor and therefore jeopardise product purity. Furthermore, any heating or cooling of such open photobioreactor systems that may be required is difficult to design. In the case of illumination exclusively with sunlight, a daytime dependence also results, deeper layers often only being illuminated unsatisfactorily, whereas directly at the surface of the open system, very high illumination intensities may occur, which may if appropriate lead to what is known as photoinhibition.

The sum of the mentioned disadvantages or limiting boundary conditions can in particular lead to it often only being possible to use open photobioreactor systems in the form of open ponds all year round in very particular geographical areas.

Closed photobioreactor systems were developed in order to reduce an influence of environmental conditions on the one hand and to achieve a higher yield during the cultivation of phototrophic organisms on the other hand. In such closed systems, a nutrient solution is conveyed through a closed circuit together with the organisms and for the most part illuminated from outside in the process.

For example, in a pipe photobioreactor, glass or plastic pipes are combined to form a closed circuit and the organisms enclosed therein are supplied with nutrients and $CO_2$ by means of a central unit, which can contain suitable pumps and sensors for example.

Closed photobioreactors generally allow a high degree of process control, because the organisms and the surrounding nutrient solution can be heated or cooled well in the closed system, a pH value can be monitored and adjusted if necessary, and additional light can be provided. The closed systems allow a high productivity for a low area requirement, because for example, a plurality of closed systems can be arranged above one another or pipes of one system can run in the vertical direction and can thereby be illuminated from all sides. Shadow effects are always to be expected, however. In addition, high product purity with low contamination, low evaporation and low electromagnetic interference (EMC) is also possible.

However, technical outlay and corresponding plant investment costs when building complex closed photobioreactors are generally very high compared to open systems.

A plurality of technical solutions have already been developed to increase the efficiency of photobioreactors. A measure for the efficiency of a photobioreactor can here be understood to be the quantity of necessary resources, such as for example energy to be supplied in the form of light and/or electricity, area to be provided, nutrients to be provided, etc. in relation to the yield of the photobioreactor in the form of biomass with the highest possible quantities of energy chemically stored therein.

For example, a photobioreactor with rotationally oscillating light sources was described in EP 2 520 642 A1.

SUMMARY

It is an object of the embodiments described herein to provide an option for being able to supply a photobioreactor for cultivating phototrophic organisms in particular both with light and with nutrients in a simple and cost-effective manner.

According to a first aspect, a specially constructed elongated hollow optical waveguide is suggested. The optical waveguide has a casing made from a transparent material, which surrounds a hollow core. The hollow core has a diameter of at least 1 mm, preferably at least 3 mm or at least 1 cm. A plurality of openings with a diameter of at least 0.5 mm, preferably at least 1 mm, possibly even at least 2 mm, is constructed in the casing.

According to a further aspect, an optical-waveguide arrangement is suggested, which has a plurality of optical waveguides according to the first aspect above.

According to yet a still further embodiment, a photobioreactor is suggested, which has a container for accommodating organisms in a solution and also an optical waveguide or optical-waveguide arrangement according to the above first or second aspect for supplying the organisms in the container with light and nutrients.

A method for operating one such photobioreactor is suggested according to a further aspect. The method comprises the introduction of light via the optical waveguide into the solution, to which organisms have been added, and also an introduction of nutrients via the hollow core of the optical waveguide into the solution, to which organisms have been added.

A method for manufacturing an optical waveguide according to the above first aspect is suggested according to a further aspect of the embodiment. In this case, initially a hollow optical waveguide with a casing made from transparent material, that surrounds a hollow core is provided, and subsequently a plurality of openings with a diameter of at least 0.5 mm is created in the casing by means of laser irradiation.

The embodiments described herein can be considered inter alia as relating to the following ideas and discoveries:

Phototrophic organisms should be supplied both with light and with nutrients as well as possible during their cultivation. For conventional, particularly closed photobioreactors, it has already been suggested to introduce light directly into the interior of a container of the photobioreactor with the aid of optical waveguides for example. In this case, the phototrophic organisms are located in the container accommodated in a nutrient solution. In order to supply the phototrophic organisms with nutrients, these nutrients are conventionally introduced into the nutrient solution in the interior of the container via various inlets. For example, gases, such as $CO_2$ for example, water and trace elements are in each case introduced via separate inlets. This generally requires a complex set-up of the photobioreactor and the various nutrient sources connected to the same.

It is suggested to simplify the set-up of a photobioreactor considerably, in that both light and nutrients can be introduced into the interior of a container of the photobioreactor by means of an optical waveguide. A specially constructed hollow optical waveguide is suggested.

Optical waveguides have hitherto principally been used to conduct light from one location to another as losslessly as possible. In this case, the optical waveguides are for example used in the form of glass fibres, mostly for data transmission. Highly transparent glass is generally used as material for such optical waveguides. In order to be able to achieve satisfactory mechanical flexibility of such an optical waveguide, the optical waveguide is generally produced as a thin fibre with an external diameter of considerably below 1 mm for the most part.

Furthermore, hollow fibres are known, as are generally used for example in the textile industry as insulating material or absorbent filling material or else for building filter modules. The casing of such hollow fibres does not have to consist of a transparent material for these use purposes, however.

It is suggested to construct an optical waveguide as a type of hollow fibre, in which on the one hand the casing consists of a transparent material and on the other hand the hollow core surrounded by the casing has a satisfactory diameter, so that nutrients can be transported through it. For this, the core should have a diameter of at least 1 mm, preferably at least 3 mm or better at least 1 cm, so that flowable nutrients can be transported through this hollow core without excessive frictional losses.

In order to not only be able to deliver the nutrients conveyed through the hollow core locally at the end of the optical waveguide, but rather, to the greatest extent possible, to be able to deliver the nutrients evenly inside a container of a photobioreactor for example, a plurality of openings are provided in the casing of the hollow optical waveguide. The hollow core of the optical waveguide is connected to the environment via these openings. A diameter of these openings should be at least 0.5 mm, preferably at least 1 mm, so that nutrients conveyed through the hollow core can flow through the openings outwards into the container easily and with as little friction as possible.

The suggested hollow optical waveguide can therefore be used in an advantageous manner to conduct or to convey both light and nutrients from one location to another. The transparent casing of the optical waveguide is in this case primarily used for conducting the light. Furthermore, it surrounds the hollow core, through which the nutrients can be conveyed. The substances conveyed in the hollow core can then escape to the outside through the openings constructed in the casing at desired locations.

In a photobioreactor, hollow optical waveguides of this type can therefore advantageously be used to introduce both light and nutrients from outside into the interior of a container of the photobioreactor.

According to an embodiment, the casing of the optical waveguide consists of plastic. A use of plastic for the casing can also assure satisfactory mechanical resilience and/or satisfactory mechanical elasticity in the case of the envisaged large diameters of the suggested optical waveguide. Any plastic or any plastic mixture, which has sufficient optical transparency along with simultaneously suitable mechanical properties for the intended use purpose, can be used for the casing. Polymethyl methacrylate (PMMA), for example POF optical waveguides (polymer optical fibre), can be used in particular as the plastic for the casing.

According to an embodiment, the casing can consist of a material which can be heated to at least 60° C. without being damaged. This means that the optical waveguide can be thermally sterilised. This may be important for use in photobioreactors in particular.

According to one embodiment, the casing is closed off at least at one end face. This has the advantage that coupling in the light is simplified by means of a closed end face. This advantage can also be achieved if the optical waveguide is solid, that is to say is not hollow, in the region of the end face. For example, the solidly constructed region extends from the end face up to 1 mm, 1 cm, 20 cm or up to 50 cm length of the optical waveguide. A further advantage of the closed end face is the fact that the exit of the gases and/or nutrients to be introduced can take place out of the openings provided therefor, for example, the introduction of the gases and/or the nutrients can be controlled, for example by means of the number of openings per length of the optical waveguide.

According to an embodiment, in an optical-waveguide arrangement with a plurality of above-described hollow optical waveguides, the optical waveguides have various external diameters. This also generally implies that the various hollow optical waveguides have different internal diameters, that is to say have hollow cores of different diameters. In this case, the different optical waveguides can be adapted to different use purposes. For example, an optical waveguide with smaller external diameter and therefore smaller hollow core can well be used to convey gaseous nutrients, such as for example $CO_2$, because frictional losses generally play a less important role here. To convey liquid nutrients, such as for example water, to which trace elements have been added, a hollow optical waveguide with a relatively large diameter and therefore a relatively large hollow core can be used by contrast, so that the liquid medium can be conveyed through the hollow core of the optical waveguide with sufficiently little friction in spite of its high viscosity compared to gases.

According to an embodiment, the optical waveguides can be combined to form a bundle. In this case, a plurality of optical waveguides can be mechanically connected to one another, for example by means of an adhesive or connecting fibres, and therefore better handled, for example.

According to an embodiment, the optical waveguides can alternatively be interwoven to form a mat. In a design of this type, which is interwoven to form a mat, the optical waveguides can be satisfactorily securely connected to one another without further auxiliary means, such as adhesives or connecting fibres for example.

For a use in a photobioreactor in particular, the suggested hollow optical waveguide can have yet further advantageous features.

For example, the casing can be provided with an additional layer on its internal surface, which is directed towards the hollow core. This additional layer can ensure chemical resistance to media conveyed through the hollow core, for example. The additional layer can also serve as a reflection layer, in order to prevent light conducted in the casing from leaving the casing by the side closest to the hollow core and then being absorbed in the medium conveyed in the hollow core and thus being lost for supplying light to the phototrophic organisms. To this end, the additional layer may be metallic for example.

The casing of the hollow optical waveguide can furthermore be designed in a targeted manner such that light conducted in the casing does not exclusively exit at the end faces of the optical waveguide, but rather a significant proportion of this light is coupled outwards in advance laterally transversely to the optical waveguide. As a result, it can be achieved for example in a bioreactor, that light is coupled into the solution accommodating the organisms not only locally and therefore with high intensity at the end of the optical waveguide, but rather the solution is irradiated with light over a larger area along the entire casing surface of the optical waveguide, for example. To this end, the external surface of the casing can be roughened in a targeted manner for example, in order to provoke a lateral coupling of the light out of the optical waveguide.

The hollow optical waveguide or the optical-waveguide arrangement, as have been described previously, can in particular be used advantageously for a photobioreactor, in order to supply organisms with light and nutrients in the same. According to an embodiment, the photobioreactor can have one light source, which is connected to at least one of the optical waveguides in such a manner that light from the light source is coupled into the optical waveguide and can be transferred via the optical waveguide into the solution, to which organisms have been added. The photobioreactor can furthermore have a nutrient source, which is connected to at least one of the optical waveguides in such a manner that nutrients from the nutrient source are introduced into the hollow core of the optical waveguide and can be transferred via the same into the solution, to which organisms have been added.

In a further embodiment, the photobioreactor can have a plurality of different nutrient sources and a plurality of different optical waveguides, each of the nutrient sources being constructed for providing a liquid or a gaseous nutrient and being connected to at least one of the optical waveguides in such a manner that nutrients from the nutrient source can be introduced to the hollow core of the optical waveguide and can be transferred via the same into the solution, to which organisms have been added. Here, it is advantageously possible to make use of the fact that a different optical waveguide with different properties can be used, depending on the type of nutrient that should be transferred from a nutrient source into the solution. For example, a hollow optical waveguide with a thinner core diameter can be used for transferring gas than is used for transferring nutrients accommodated in a liquid solution.

According to a further embodiment, the photobioreactor can furthermore have a suction device, which is constructed such and connected to at least one of the optical waveguides in such a manner that with the aid thereof, a solution to which organisms have been added can be sucked out of the container through the hollow core of the optical waveguide and subsequently provided for an analysis of the solution, to which organisms have been added. In other words, the hollow optical waveguide can not only be provided to introduce light and nutrients into the container of the photobioreactor, rather also in the reverse direction, nutrient solution, to which organisms have been added, can be removed from the container via the hollow optical waveguide, in order to be able to analyse the same.

It is pointed out that possible advantages and features of embodiments are described herein, to some extent with reference to a hollow optical waveguide according to an embodiment, to some extent with reference to an optical-waveguide arrangement according to an embodiment, to some extent with reference to a photobioreactor according to an embodiment, to some extent with reference to a method for operating one such photobioreactor, and to some extent with reference to a method for manufacturing an optical waveguide. A person skilled in the art will recognise that the various features can be combined, exchanged or analogously transferred in a suitable manner in order to realise further embodiments.

BRIEF DESCRIPTION OF THE DRAWINGS

The various embodiments will hereinafter be described in conjunction with the following drawing figures, wherein like numerals denote like elements, and.

The figures are only schematic and not true to scale. Identical reference numbers in the different figures designate identical or identically acting features.

DETAILED DESCRIPTION

The following detailed description is merely exemplary in nature and is not intended to limit the disclosed embodiments or the application and uses thereof. Furthermore, there is no intention to be bound by any theory presented in the preceding background detailed description.

Figure 1:
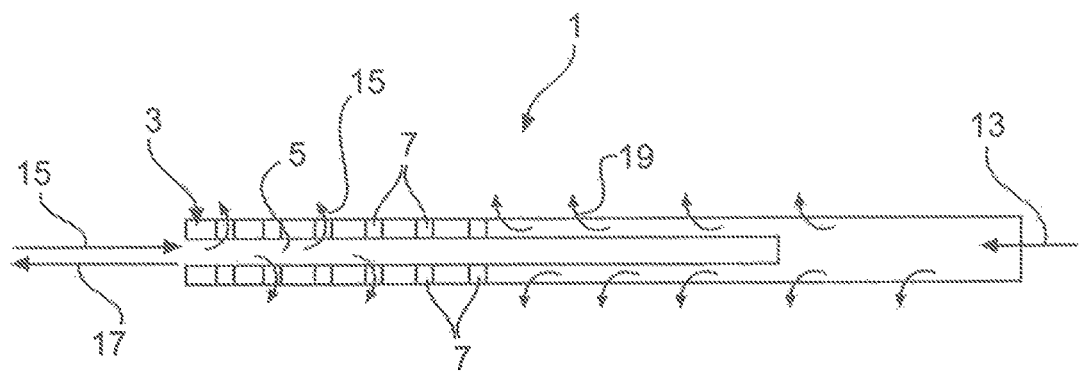
FIG. 1 shows a cross-sectional view of a hollow optical waveguide according to an embodiment.
Figure 2:
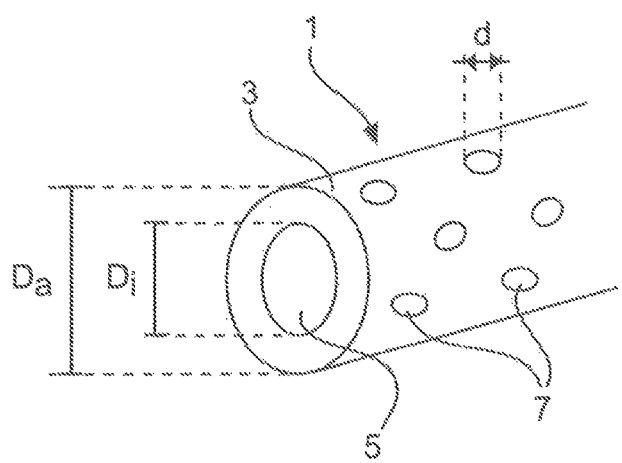
FIG. 2 shows a perspective view of a hollow optical waveguide according to an embodiment.

FIGS. 1 and 2 respectively illustrate a cross-sectional view and a perspective view of an elongated hollow optical waveguide 1 according to an embodiment. The optical waveguide 1 has a casing 3 made from transparent plastic, which surrounds a hollow core 5. The casing 3 is cylindrical and has an external diameter $D_a$ of 1 cm for example. An internal diameter $D_i$ of the casing 3 corresponds to the diameter of the hollow core 5 and is 0.5 cm for example.

A plurality of continuous openings 7 are formed in the casing 3 of the optical waveguide 1, at least in a part region, by means of which openings, the hollow core 5 is connected to the environment and in particular can exchange fluids. The openings 7 have a diameter d of at least 0.5 mm for example. The openings 7 are arranged spaced from one another in the casing in this case, a distance between adjacent openings 7 preferably being considerably larger than the diameter d of the openings 7, in order to not excessively weaken the stability of the optical waveguide 1.

In the example illustrated in FIG. 1, the casing 3 of the optical waveguide 1 is closed off at an end face (on the right side in FIG. 1).

The optical waveguide 1 can for example be used in a photobioreactor, in order to be able to introduce both light 13 and nutrients 15 from outside into a container in the interior of the photobioreactor.

In this case, the light 13 is coupled into the optical waveguide 1, particularly into the casing 3 thereof, coming from a light source, and can then propagate along the optical waveguide 1, in a manner similar to that in the case of conventional optical waveguides. The optical waveguide 1 is in this case adapted in a targeted fashion such that the light 13 does not propagate completely from one end to the other end through the optical waveguide 1, rather, it is coupled along the optical waveguide 1 successively and preferably continuously outwards out of the casing 3, as indicated in FIG. 1 by the arrows 19. The light 13 therefore does not need to be coupled out locally at the end of the optical waveguide 1, rather it can be coupled out along the entire external surface of the casing 3 and therefore illuminate the solution, which is contained in the container of the photobioreactor and to which organisms have been added, over a large area.

In a similar manner, the openings 7 are preferably evenly distributed over the casing 3 of the optical waveguide 1, so that the nutrients 15 transferred in the hollow core 5 can preferably exit outwards evenly through the plurality of openings 7 along the length of the optical waveguide 1 and the organisms contained in the surrounding solution can be supplied.

Both light and nutrients, for example in the form of gases, liquids and trace elements dissolved therein, can then be introduced into a photobioreactor simultaneously with the aid of the optical waveguide 1. Likewise, nutrient solution, to which organisms have been added, can be sucked out of the container of the bioreactor in the reversed direction, as indicated by the arrow 17, in order to be able to analyse it externally for example.

Figure 3:
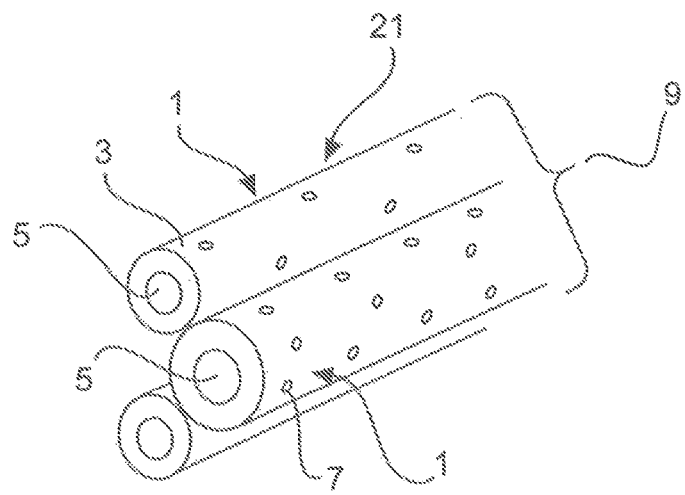
FIG. 3 shows a perspective view of an optical-waveguide arrangement according to an embodiment.

An optical-waveguide arrangement 21 according to an embodiment is illustrated in FIG. 3. The optical-waveguide arrangement 21 has a bundle 9 made up of a plurality of optical waveguides 1. In this case, the optical waveguides 1 have different external diameters. Gases, such as for example $CO_2$, can for example be conveyed through the cores 5 of optical waveguides 1 of smaller diameter, whereas liquids can also be conveyed through the hollow core 5 of an optical waveguide 1 with a larger diameter. Both the gases and the liquids can exit outwards through the openings 7 into a nutrient solution present in the photobioreactor for example.

Figure 4:
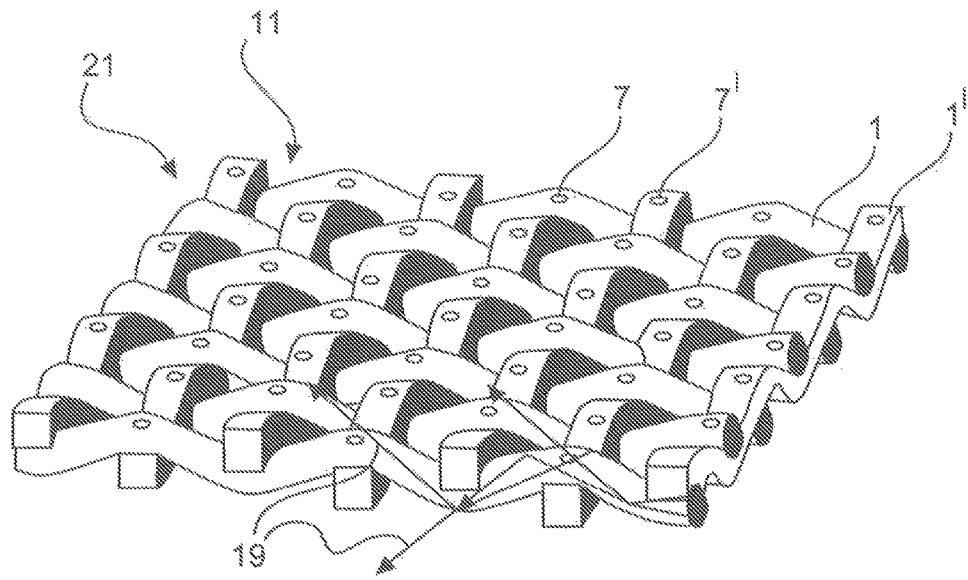
FIG. 4 shows a perspective view of a woven optical-waveguide arrangement according to a further embodiment.

FIG. 4 shows an alternative design of an optical-waveguide arrangement 21, in which a plurality of optical waveguides 1 are interwoven to form a mat 11. The same or different types of optical waveguides 1 can be used in the warp and weft direction, wherein the optical waveguides 1 can differ with regards to their diameter in particular. Particularly in regions in which the optical waveguides 1 are most curved inside the fabric 11, local coupling out of light guided in the optical waveguides 1 may occur, as indicated in turn with the arrows 19, so that light can preferably be coupled out across the entire mat 11 and transversely to the surface thereof. In this manner, a nutrient solution can be illuminated over a large area in a photobioreactor, for example.

Figure 5:
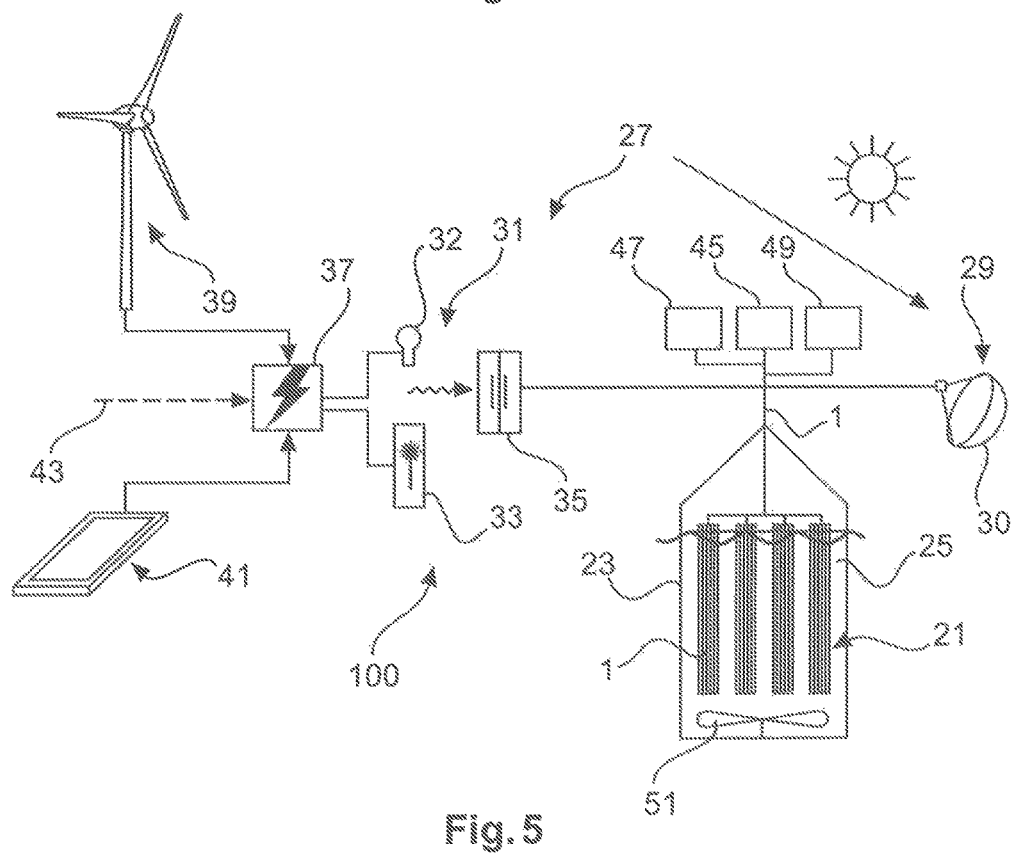
FIG. 5 shows a photobioreactor according to an embodiment.

FIG. 5 schematically shows a photobioreactor 100 according to an embodiment. The photobioreactor 100 has a container 23, in which phototrophic organisms can be accommodated in a solution 25. A plurality of optical waveguides 1 are accommodated in the container 23, in order to be able to supply the phototrophic organisms both with light and with nutrients. The photobioreactor 1 furthermore has at least one light source 27 and at least one nutrient source 45, 47.

The light source 27 can have one or a plurality of components for artificially generating light or for collecting naturally generated light and subsequent coupling of this light into a common optical waveguide 1 for supplying the bioreactor 100. On the one hand, the light source 27 can be designed as a light source 29 for collecting and coupling sunlight into the optical waveguide. To this end, the light source 29 can for example be designed as a solar collector 30 with a hollow mirror, which focusses sunlight onto a receiver. Additionally or alternatively, the light source 27 can be constructed as an artificial light source 31, in which light is generated with the aid of an LED 32 or a laser 33, for example, which light is subsequently irradiated onto an arrangement 35 made up of a polariser and a screen, which arrangement is in turn connected to the optical waveguide 1 towards the container 23 of the photobioreactor 1. The artificial light source 31 can in this case be supplied with electric power from alternative sources, such as wind power 39 or solar cells 41 or alternatively by means of conventional power 43, for example. The electric power can here be buffer stored by means of a buffer battery 37, for example, so that the artificial light source 31 can illuminate the photobioreactor 100, even in the case of insufficient sunshine.

According to an embodiment, the optical waveguides 1 are not only used for transferring light received from the light source 27 into the interior of the container 23 and the solution 25 contained therein, to which organisms have been added. In addition, nutrient sources 45, 47 are connected to the optical waveguides 1 and in particular to the hollow core 5 thereof. From these nutrient sources 45, 47, $CO_2$ a nutrient solution containing further nutrients is fed into the interior of the hollow optical waveguide 1 and then transferred via the hollow core 5 into the container 23. There, the nutrients can exit from hollow optical waveguides 1 via the openings 7.

In a reversal of the flow direction, the hollow optical waveguides 1 can also be used to suck a solution 25, to which organisms have been added, out of the container 23 by means of a suction device 49, in order to be able to analyse the solution. The solution 25 is in this case sucked through the openings 7 in the optical waveguides 1 in the core 5 thereof, and then pumped out of the interior of the container 23, for example to an analysing apparatus.

In order to be able to distribute the nutrients exiting from the hollow optical waveguides 1 evenly inside the entire container 23, an agitator 51 is furthermore provided, with the aid of which the solution 25 can be permanently circulated.

In order to produce a hollow optical waveguide according to an embodiment, an optical waveguide, in which a casing 3 made from transparent material surrounds a hollow core 5, is initially provided. Here, the hollow core 5 should preferably have a diameter of at least 1 mm, more preferably of at least 3 mm or 1 cm. Subsequently, a plurality of openings 7 can be created in the casing 3 of the optical waveguide 1. To this end, the casing can locally be irradiated with a laser of sufficient power density, so that material of the casing 3 is removed locally and the openings 7 result. A diameter and a power of the laser used therefor can be chosen in a suitable manner such that openings with a diameter of at least 0.5 mm are formed. If the optical waveguide 1 is already hollow in this processing stage, then two openings 7 in opposite regions of the casing 3 can be created simultaneously using single laser irradiation.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the embodiment in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the embodiment as set forth in the appended claims and their legal equivalents.

What is claimed is:

1. A photobioreactor comprising:
    a container for accommodating organisms in a solution;
    at least one optical waveguide having a transparent material and being configured to guide light, the at least one optical waveguide extending into the container and configured to supply the organisms in the container with light, wherein a hollow core is formed by the transparent material to supply the organisms in the container with nutrients, wherein the nutrients transferred in the hollow core exit the at least one optical waveguide outwards and into the solution surrounding the at least one optical waveguide in the container;
    a light source, coupled to the at least one of the optical waveguides in such a manner that light from the light source is coupled into the transparent material of the optical waveguide and can be transferred via the optical waveguide into a solution, to which solution organisms have been added, and
    a nutrient source, which is connected to at least one of the optical waveguides in such a manner that nutrients from the nutrient source are introduced into the hollow core of the optical waveguide and can be transferred via the same into the solution, to which solution organisms have been added.

2. The photobioreactor according to claim 1, wherein the transparent material comprises plastic.

3. The photobioreactor according to claim 1, wherein the transparent material comprises a material that can be heated to at least 60° C. without being damaged.

4. The photobioreactor according to claim 1, wherein the transparent material is closed off at least at one end.

5. The photobioreactor according to claim 1, wherein the at least one optical waveguide comprises a plurality of optical waveguides having different external diameters.

6. The photobioreactor according to claim 1, wherein the at least one optical waveguide comprises a plurality of optical waveguides combined to form a bundle.

7. The photobioreactor according to claim 1, wherein the at least one optical waveguide comprises a plurality of optical waveguides interwoven with one another to form a mat.

8. The photobioreactor according to claim 1, comprising:
    a plurality of different nutrient sources and a plurality of different optical waveguides, wherein each of the nutrient sources is configured for providing a liquid or a gaseous nutrient and is coupled to at least one of the optical waveguides in such a manner that nutrients from the nutrient source can be introduced into the hollow core of the optical waveguide and can be transferred via the same into the solution, to which solution organisms have been added.

9. The photobioreactor according to claim 1, further comprising,
    a suction device, which is configured to be connected to at least one of the optical waveguides in such a manner in order to suck a solution, to which solution organisms have been added, out of the container through the hollow core of the optical waveguide and provide the same for an analysis of the solution, to which solution organisms have been added.

10. A method for operating a photobioreactor comprising a container for accommodating organisms in a solution, and further comprising at least one optical waveguide having a transparent material and being configured to guide light, the at least one optical waveguide extending into the container and configured to supply the organisms in the container with light, wherein a hollow core is formed by the transparent material to supply the organisms in the container with nutrients, wherein the nutrients transferred in the hollow core exit the at least one optical waveguide outwards and into the solution surrounding the at least one optical waveguide in the container, the method comprising the steps of:
    introducing light via the at least one optical waveguide into the solution, to which solution organisms have been added, and introducing nutrients via the hollow core of the at least one optical waveguide into the solution, to which solution organisms have been added.

11. The method according to claim 10, further comprising:
suctioning of a solution, to which solution organisms have been added, out of the container through the hollow core of the at least one optical waveguide; and
providing the same for an analysis of the solution, to which solution organisms have been added.

12. A photobioreactor comprising:
a container for accommodating organisms in a solution;
an optical waveguide having a transparent material, wherein a hollow core is formed by the transparent material; and
a nutrient source connected to the optical waveguide such that nutrients from the nutrient source are introduced into the hollow core of the optical waveguide and can be transferred via the optical waveguide into the solution;
the optical waveguide extending into the container and configured to guide light and to supply the organisms in the container with light, wherein the hollow core is formed to supply the organisms in the container with nutrients, wherein the nutrients transferred in the hollow core exit the optical waveguide outwards and into the solution surrounding the optical waveguide in the container.

* * * * *